United States Patent
Müller et al.

(10) Patent No.: US 8,471,076 B2
(45) Date of Patent: Jun. 25, 2013

(54) PROCESS AND PLANT FOR PRODUCING METHANOL

(75) Inventors: Dierk Müller, Karben (DE); Andreas Bormann, Frankfurt am Main (DE)

(73) Assignee: Lurgi GmbH, Frankfurt am Main (DE)

( * ) Notice: Subject to any disclaimer, the term of this patent is extended or adjusted under 35 U.S.C. 154(b) by 395 days.

(21) Appl. No.: 12/674,460

(22) PCT Filed: Aug. 18, 2008

(86) PCT No.: PCT/EP2008/006759
§ 371 (c)(1),
(2), (4) Date: Dec. 2, 2010

(87) PCT Pub. No.: WO2009/030353
PCT Pub. Date: Mar. 12, 2009

(65) Prior Publication Data
US 2011/0065966 A1    Mar. 17, 2011

(30) Foreign Application Priority Data

Aug. 29, 2007  (DE) .................. 10 2007 040 707

(51) Int. Cl.
*C07C 29/151*  (2006.01)
*C07C 29/152*  (2006.01)
*B01J 8/04*  (2006.01)
*B01J 8/06*  (2006.01)

(52) U.S. Cl.
USPC ........... 568/884; 568/840; 568/885; 518/700; 518/705; 518/706; 518/707

(58) Field of Classification Search
USPC ......................................... 568/884
See application file for complete search history.

(56) References Cited

U.S. PATENT DOCUMENTS

| 5,631,302 | A  | * | 5/1997  | Konig et al. ................. | 518/706 |
| 5,827,901 | A  | * | 10/1998 | Konig et al. ................. | 518/706 |
| 6,191,175 | B1 | * | 2/2001  | Haugaard et al. ............ | 518/705 |
| 6,387,963 | B1 | * | 5/2002  | Fitzpatrick .................... | 518/706 |
| 6,433,029 | B1 | * | 8/2002  | Fitzpatrick .................... | 518/706 |
| 7,790,775 | B2 | * | 9/2010  | Early ............................. | 518/706 |

FOREIGN PATENT DOCUMENTS

| CA | 2197574 | 11/2005 |
| EP | 0790226 | 8/1997  |
| EP | 1026141 | 8/2000  |

OTHER PUBLICATIONS

International Search Report for Application PCT/EP2008/006759, mailed Oct. 14, 2008, 4 pages.

* cited by examiner

*Primary Examiner* — Brian J Davis
(74) *Attorney, Agent, or Firm* — Pauly, Devries Smith & Deffner, L.L.C.x

(57) ABSTRACT

In the production of methanol from a synthesis gas containing hydrogen and carbon oxides, the synthesis gas is passed through a first, preferably water-cooled reactor, in which a part of the carbon oxides is catalytically converted to methanol. The obtained mixture containing synthesis gas and methanol vapor is supplied to a second, preferably gas-cooled reactor, in which a further part of the carbon oxides is converted to methanol. Subsequently, methanol is separated from the synthesis gas, and the synthesis gas is recirculated to the first reactor. To achieve a maximum methanol yield even with an aged catalyst, a partial stream of the synthesis gas is guided past the first reactor and introduced directly into the second reactor.

9 Claims, 1 Drawing Sheet

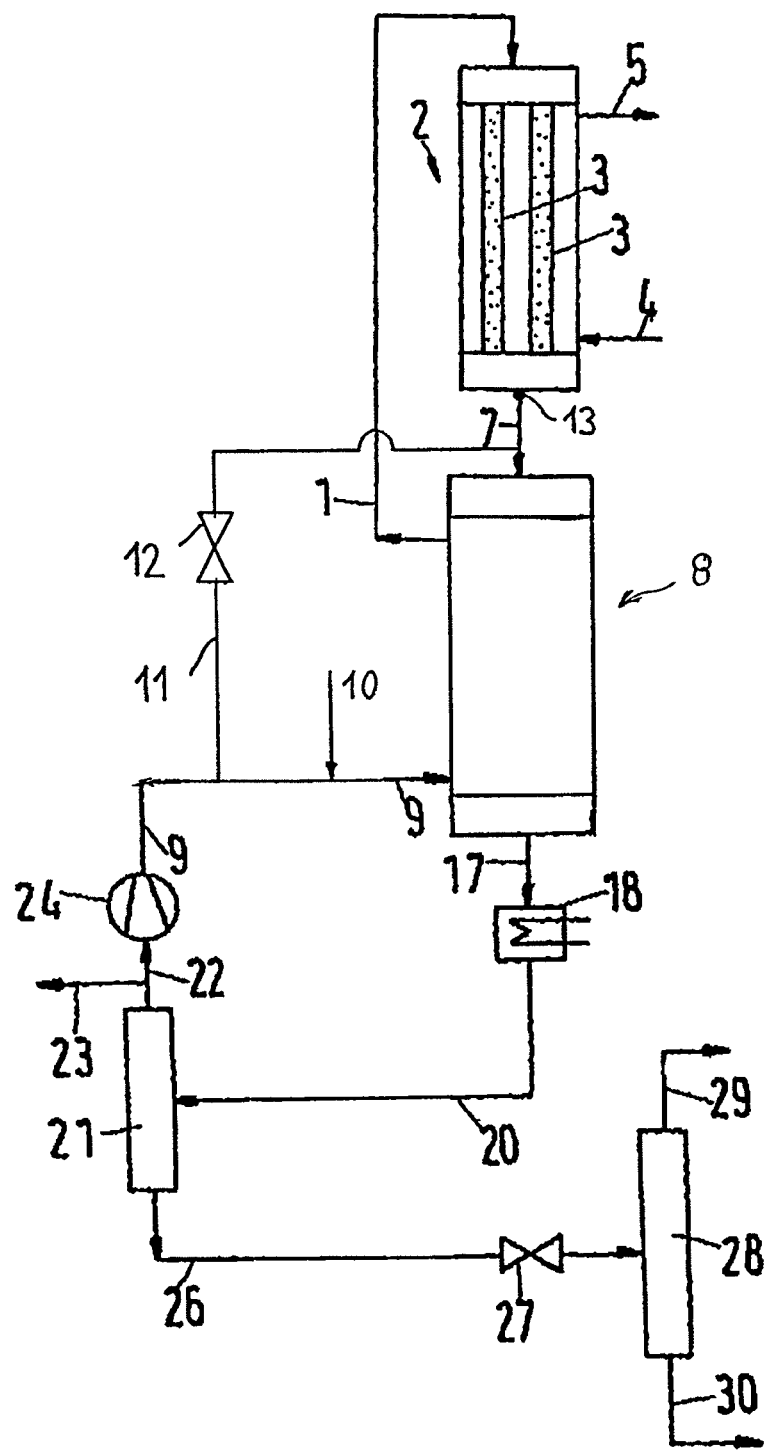

PROCESS AND PLANT FOR PRODUCING METHANOL

CROSS-REFERENCE TO RELATED APPLICATIONS

This application is a national stage application under 35 U.S.C. 371 of International Patent Application Serial No. PCT/EP2008/006759, entitled "Verfahren and Anlage zur Herstellung von Methanol," filed Aug. 18, 2008, which claims priority from German Patent Application No. 10 2007 040 707.8, filed Aug. 29, 2007.

FIELD OF THE INVENTION

This invention relates to the production of methanol from a synthesis gas containing hydrogen and carbon oxides, wherein the synthesis gas is passed through a first, preferably water-cooled reactor, in which a part of the carbon oxides is catalytically converted to methanol, wherein the obtained mixture containing synthesis gas and methanol vapor is supplied to a second, preferably gas-cooled reactor, in which a further part of the carbon oxides is catalytically converted to methanol, wherein methanol is separated from the synthesis gas and wherein synthesis gas is recirculated to the first reactor.

BACKGROUND OF THE INVENTION

Such process for producing methanol is known for instance from EP 0 790 226 B1. The methanol is produced in a cyclic process, in which a mixture of fresh and partly reacted synthesis gas is first supplied to a water-cooled reactor and then to a gas-cooled reactor, in which the synthesis gas is each converted to methanol on a copper catalyst. The methanol produced in the process is separated from the synthesis gas to be recirculated, which then is passed through the gas-cooled reactor as coolant and preheated to a temperature of 220 to 280° C., before it is introduced into the first synthesis reactor. The maximum yield of methanol in the gas-cooled, second reactor, which is determined by the thermodynamics, greatly depends on the temperature profile in the reactor and on the outlet temperature thereof. If the water-cooled first reactor is filled with fresh catalyst, a large part of the carbon oxides in the water-cooled reactor is converted. However, the amount of carbon oxides converted in the water-cooled reactor decreases with the ageing of the catalyst, which leads to the fact that a large part of the total conversion of methanol takes place in the gas-cooled reactor. In order to counter the effect of ageing of the catalyst in the water-cooled reactor, the outlet temperature from the first reactor and hence the inlet temperature into the second reactor is increased. An increase in temperature, however, causes a shift of the reaction equilibrium towards the educts in the gas cooled reactor, which means a reduction of the maximum methanol yield to be achieved.

SUMMARY OF THE INVENTION

It is the object of the invention to achieve a high methanol yield of the process also with an aged catalyst.

In a process as mentioned above, this object substantially is solved in that a partial stream of the synthesis gas is guided past the first reactor and introduced directly into the second reactor. By means of the synthesis gas guided past the first reactor, which preferably together with the gas mixture withdrawn from the water-cooled first reactor is introduced into the second reactor, the temperature of the gas mixture withdrawn from the first reactor can be decreased, so that the carbon conversion in the second reactor is increased. The decrease in temperature is limited by the ignition temperature of the catalyst, which in the conventionally used copper catalysts is about 220° C.

In accordance with a preferred aspect of the invention, the partial stream guided past the first reactor is branched off from the synthesis gas recirculated after the methanol separation. After the separation of methanol, said synthesis gas usually has a temperature of about 60° C., so that an efficient decrease in temperature of the gas mixture entering the second reactor is achieved. It is, however, also possible in principle to use fresh synthesis gas for the bypass, which due to its usually distinctly higher temperature of about 160° C. only provides for a correspondingly smaller decrease in temperature of the gas mixture introduced into the second reactor and requires a correspondingly larger bypass stream.

In accordance with a development of the invention, the amount of the partial stream guided past the first reactor lies in the range from 0 to 20 vol-%, preferably 5 to 15 vol-%, and in particular is about 10 vol-% of the recirculated synthesis gas. In this way, the desired inlet temperature of the gas mixture at the second reactor can be achieved.

To counter the passivation of the ageing catalyst in the first reactor, the temperature in the reactor is raised deliberately by increasing the vapor pressure. As a result, the outlet temperature of this reactor is also increased. In accordance with a particularly preferred aspect it is therefore provided that the size of the partial stream guided past the first reactor is controlled in dependence on the temperature of the gas mixture at the outlet of the first reactor. As a result, an optimum adaptation of the inlet temperature of the second reactor to the condition of the first reactor is achieved, so that a maximum methanol yield becomes possible.

The synthesis gas recycling stream guided past the first reactor as bypass is supplied to the first reactor together with fresh synthesis gas, wherein the amount of the fresh synthesis gas preferably is about 15 to 40 vol-%.

To achieve a suitable inlet temperature for the first reactor, the synthesis gas is introduced into the second reactor as coolant and thereby preheated. Additional heating means can be avoided thereby.

This invention also extends to a plant for producing methanol from a synthesis gas containing hydrogen and carbon oxide, which is suitable in particular for performing the process of the invention as described above and includes a first, preferably water-cooled reactor, in which a part of the carbon oxides is catalytically converted to methanol, a second, preferably gas-cooled reactor, to which the gas mixture obtained from the first reactor is supplied via a conduit and in which a further part of the carbon oxides is catalytically converted to methanol, a separating means for separating the methanol from the synthesis gas, and a return conduit for recirculating synthesis gas to the first reactor. In accordance with the invention, a bypass conduit for synthesis gas leads past the first reactor to the inlet of the second reactor.

To be able to adjust the inlet temperature (control variable) of the second reactor to a value suitable for the maximum recovery of methanol, a control valve is provided in accordance with the invention for influencing the size of the gas stream (actuating variable) flowing through the bypass conduit. The control preferably is effected by means of the temperature at the outlet of the first reactor (measured variable), which is detected by a temperature sensor.

Developments, advantages and possible applications of the invention can be taken from the following description of an embodiment and the drawing. All features described and/or illustrated per se or in any combination form the subject-matter of the invention, independent of their inclusion in the claims or their back-reference.

BRIEF DESCRIPTION OF THE FIGURES

FIG. 1. schematically shows a plant for performing the process of the invention.

DETAILED DESCRIPTION

In the plant shown in FIG. 1, a mixture of fresh and recirculated synthesis gas is passed through a conduit 1 into a first synthesis reactor 2. This first reactor 2 is a tubular reactor known per se, in which for instance a copper catalyst is arranged in tubes 3. Water boiling under an elevated pressure is used as coolant, which is supplied in conduit 4. A mixture of boiling water and steam is withdrawn in conduit 5 and supplied to a non-illustrated steam drum known per se for recovering energy.

The synthesis gas entering the first reactor 2 is preheated to a temperature >220° C., since the catalyst does not respond below this temperature. Usually, the gas temperature at the inlet of the first reactor 2 is about 220 to 280° C., and the pressure lies in the range from 2 to 12 MPa (20 to 120 bar), preferably in the range from 3 to 10 MPa (30 to 100 bar) and in particular in the range from 4 to 10 MPa (40 to 100 bar). The coolant, which is withdrawn via conduit 5, usually has a temperature in the range from 240 to 280° C. In the first reactor 2, 40 to 80% of the carbon oxides supplied to the reactor 2 through conduit 1 are converted in an exothermal reaction, depending on the condition of the catalyst.

From the first reactor 2, a first mixture substantially consisting of synthesis gas and methanol vapor is withdrawn via conduit 7, wherein the methanol content is 4 to 10 vol-%, mostly 5 to 8 vol-%. This mixture is introduced into the second synthesis reactor 8, which for instance likewise is configured as a tubular reactor with a copper catalyst. Like in the first reactor 2, the catalyst can be provided in the tubes or preferably on the shell side.

As cooling medium, synthesis gas is used in the second reactor 8, which is supplied via conduit 9 with a temperature of 80 to 130° C. Fresh synthesis gas, which is produced in a non-illustrated plant known per se, is supplied via conduit 10 and admixed to the synthesis gas to be recirculated. The temperature of the cooling gas at the inlet of the second reactor 8 results from the mixing ratio between recirculated and fresh synthesis gas and is chosen the lower the higher the inlet temperature of the first mixture into the second reactor 8. The synthesis gas used as coolant is preheated in the second reactor 8 and then flows through conduit 1 to the first reactor 2.

The synthesis gas which enters the first reactor 2 should include hydrogen and carbon oxides in about the following amounts:

$H_2$=40 to 80 vol-%
CO=3 to 15 vol-%, and
$CO_2$=1 to 10 vol-%.

A product mixture substantially containing synthesis gas and methanol vapor (second mixture) leaves the second reactor 8 through a conduit 17 and flows through an indirect cooler 18, wherein methanol is condensed. Subsequently, the mixture is charged through conduit 20 into a first separating tank 21, in which gases and liquid are separated. The gases are withdrawn through conduit 22, wherein part of the gases can be removed from the process via a conduit 23. By means of the condenser 24, the gases are passed as synthesis gas to be recirculated (recycle gas) through the second reactor 8 via conduit 9, and after the preheating effected thereby they are passed on into the first reactor 2. Via a bypass conduit 11, a partial stream of the recirculated synthesis gas is branched off and supplied past the first reactor 2 directly to the inlet region of the second reactor 8. This partial stream, which usually has a temperature of 50 to 100° C., is mixed in conduit 7 with the first mixture emerging from the first reactor 2 and thereby decreases the temperature of the same.

The size of the partial stream guided through the bypass conduit 11 is controlled via a control valve 12 provided in particular in the bypass conduit 11, wherein the control is effected on the basis of the outlet temperature detected by a temperature sensor 13 on the outlet of the first reactor 2. In accordance with the invention, the size of the partial stream is adjusted such that it is increased starting with 0 vol-%, i.e. without bypass stream, (fresh catalyst in the first reactor 2) up to an amount of 15 or 20 vol-%, preferably, however, about 10 vol-% of the synthesis gas stream recirculated via conduit 9 (with an aged catalyst in the first reactor 2).

From the first separating tank 21, methanol-containing liquid is withdrawn via a conduit 26, and the liquid is passed through an expansion valve 27 to a second separating tank 28. Via a conduit 29, residual gas is withdrawn therefrom, while crude methanol is obtained via conduit 30, which is now cleaned by distillation in a non-illustrated manner known per se.

It should be appreciated that the configuration of the reactors 2, 8 as such is not restricted to the variants described above. Rather, modifications of these reactors are also possible, as described for instance in EP 0 790 226 B1.

EXAMPLE

Via conduit 9, a mixture of recirculated synthesis gas and fresh synthesis gas is supplied to the second reactor 8 as cooling gas. The recirculated synthesis gas has a temperature of about 60° C., whereas the fresh synthesis gas has a temperature of about 160° C. The mixing ratio initially is chosen such that a mixing temperature of about 120° C. is obtained. When the gas outlet temperature of the first reactor 2 is increased, the mixing temperature of the cooling gas at the lower inlet of the second reactor 8 can for instance also be decreased to 90° C., in order to compensate the higher temperature of the synthesis gas. Upon traversing the gas-cooled reactor 8 as coolant, the temperature of the synthesis gas which is introduced into the water-cooled first reactor 2 via conduit 1 with a pressure of about 8 MPa (80 bar) is increased to about 230 to 240° C., in any case greater than 220° C. Due to the exothermal reaction and simultaneous cooling in the first reactor 2, the first mixture of synthesis gas and methanol vapor emerges from the first reactor 2 with a temperature of 220 to 230° C. Over the first reactor 2, a pressure loss of about 0.2 MPa (2 bar) is obtained. With the ageing of the catalyst, this outlet temperature can be increased to e.g. 270° C. By admixing an amount of up to 10% of the recirculated synthesis gas, which rises corresponding to the gas outlet temperature of the first reactor 2, via the bypass conduit 11, the temperature of the gas mixture entering the gas-cooled second reactor 8 via conduit 1 is decreased to about 230 to 240° C. Upon traversing the second reactor 8, the second mixture of methanol vapor and synthesis gas has a temperature of about 220° C. and a pressure of about 7.5 MPa (75 bar). Even with an increase in the outlet temperature of the first reactor 2, the inlet temperature of the synthesis gas into the second reactor 8 thus can be adjusted such that a maximum methanol yield is achieved.

LIST OF REFERENCE NUMERALS

1 conduit
2 first reactor
3 tubes
4 conduit
5 conduit
7 conduit
8 second reactor
9 conduit
10 conduit
11 bypass conduit
12 control valve
13 temperature sensor
17 conduit
18 cooler
20 conduit
21 separating tank
22 conduit
23 conduit
24 condenser
26 conduit
27 expansion valve
28 second separating tank
29 conduit
30 conduit

The invention claimed is:

1. A process for producing methanol from a synthesis gas containing hydrogen and carbon oxides, wherein the synthesis gas is passed through a first reactor, in which a part of the carbon oxides is catalytically converted to methanol, wherein the obtained mixture containing synthesis gas and methanol vapor is supplied to a second reactor, in which a further part of the carbon oxides is converted to methanol, wherein methanol is separated from the synthesis gas and wherein synthesis gas is recirculated to the first reactor, characterized in that a partial stream of the synthesis gas is guided past the first reactor and introduced into the second reactor.

2. The process according to claim 1, characterized in that the partial stream guided past the first reactor is branched off from the synthesis gas recirculated after the separation of methanol.

3. The process according to claim 1, characterized in that the amount of the partial stream guided past the first reactor lies in a range from 0 to 20 vol-% of the recirculated synthesis gas.

4. The process according to claim 1, characterized in that the size of the partial stream guided past the first reactor is controlled in dependence on the temperature of the gas mixture at the outlet of the first reactor.

5. The process according to claim 1, characterized in that the recirculated synthesis gas is supplied to the first reactor together with fresh synthesis gas, and that the amount of the fresh synthesis gas is about 15 to 40 vol-%.

6. The process according to claim 1, characterized in that the synthesis gas is introduced into the second reactor as coolant and is thereby preheated.

7. The process according to claim 1, wherein the first reactor comprises a water cooled reactor.

8. The process according to claim 1, wherein the second reactor comprises a gas-cooled reactor.

9. The process according to claim 1, characterized in that the amount of the partial stream guided past the first reactor lies in a range from 5 to 15 vol-%, of the recirculated synthesis gas.

* * * * *